(12) United States Patent
Pralle et al.

(10) Patent No.: US 7,777,887 B2
(45) Date of Patent: Aug. 17, 2010

(54) ABSORPTION SPECTROSCOPY APPARATUS AND METHOD

(75) Inventors: Martin U. Pralle, Wayland, MA (US); Irina Puscasu, Somerville, MA (US); Peter Flowers, Milton, MA (US)

(73) Assignee: Ion Optics, Inc., Billerica, MA (US)

( * ) Notice: Subject to any disclaimer, the term of this patent is extended or adjusted under 35 U.S.C. 154(b) by 308 days.

(21) Appl. No.: 12/101,557

(22) Filed: Apr. 11, 2008

(65) Prior Publication Data

US 2008/0252892 A1  Oct. 16, 2008

Related U.S. Application Data

(60) Provisional application No. 60/923,387, filed on Apr. 13, 2007, provisional application No. 60/931,463, filed on May 22, 2007.

(51) Int. Cl.
*G01N 21/00* (2006.01)
(52) U.S. Cl. .................................. 356/440; 356/432
(58) Field of Classification Search .................. 356/300, 356/432, 440, 451
See application file for complete search history.

(56) References Cited

U.S. PATENT DOCUMENTS

| | | | |
|---|---|---|---|
| 4,322,621 A | 3/1982 | Aagard | |
| 4,557,603 A * | 12/1985 | Oehler et al. | 356/418 |
| 4,687,342 A | 8/1987 | Betzler et al. | |
| 4,749,276 A | 6/1988 | Bragg et al. | |
| 5,009,493 A * | 4/1991 | Koch et al. | 359/858 |
| 5,220,402 A | 6/1993 | Harvey | |
| 5,401,966 A | 3/1995 | Gray et al. | |
| 5,440,143 A | 8/1995 | Carangelo et al. | |
| 5,459,566 A | 10/1995 | Pearson et al. | |
| 5,485,276 A | 1/1996 | Bien et al. | |
| 5,714,759 A | 2/1998 | Nelson | |
| 5,726,752 A | 3/1998 | Uno et al. | |
| 5,731,583 A | 3/1998 | Bailey et al. | |
| 5,818,578 A | 10/1998 | Inman et al. | |
| 5,949,537 A | 9/1999 | Inman et al. | |
| 6,373,056 B1 | 4/2002 | Johnson et al. | |
| 6,528,792 B2 | 3/2003 | Johnson et al. | |
| 6,921,899 B2 * | 7/2005 | Martin | 250/349 |

(Continued)

OTHER PUBLICATIONS

International Search Report under the Patent Cooperation Treaty PCT/US08/04703, mailed Jul. 30, 2008.

*Primary Examiner*—Roy Punnoose
(74) *Attorney, Agent, or Firm*—Foley & Lardner, LLP

(57) ABSTRACT

An absorption spectroscopy apparatus including an elliptical mirror centered on the midpoint between a source/detector and a mirror. The cavity between the elliptical mirror and the source/bolometer and mirror defines an interior volume of a sample cell. Electromagnetic radiation from the source/detector travels along a multi-segment path starting from the source/bolometer toward the elliptical mirror, reflecting off of the elliptical mirror and traveling toward the mirror, reflecting off of the mirror and traveling back toward the elliptical mirror and finally reflecting off the elliptical mirror for a second time and returning toward the source/bolometer. The multiple reflections combined with the focusing effects of the elliptical mirrored surface result in an efficient sampling device. Among other aspects and advantages, the apparatus of the present disclosure is able to use incoherent, non-collimated light sources while maintaining high optical throughput efficiencies.

19 Claims, 12 Drawing Sheets

U.S. PATENT DOCUMENTS 7,564,365 B2 * 7/2009 Marman et al. ............ 340/628
2002/0185603 A1 12/2002 Daly et al.
2003/0203352 A1 10/2003 Haviland et al.

* cited by examiner

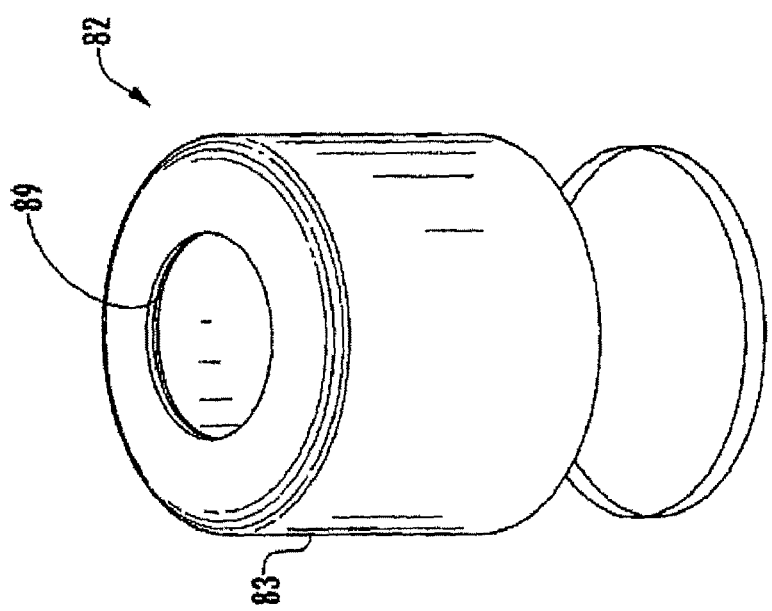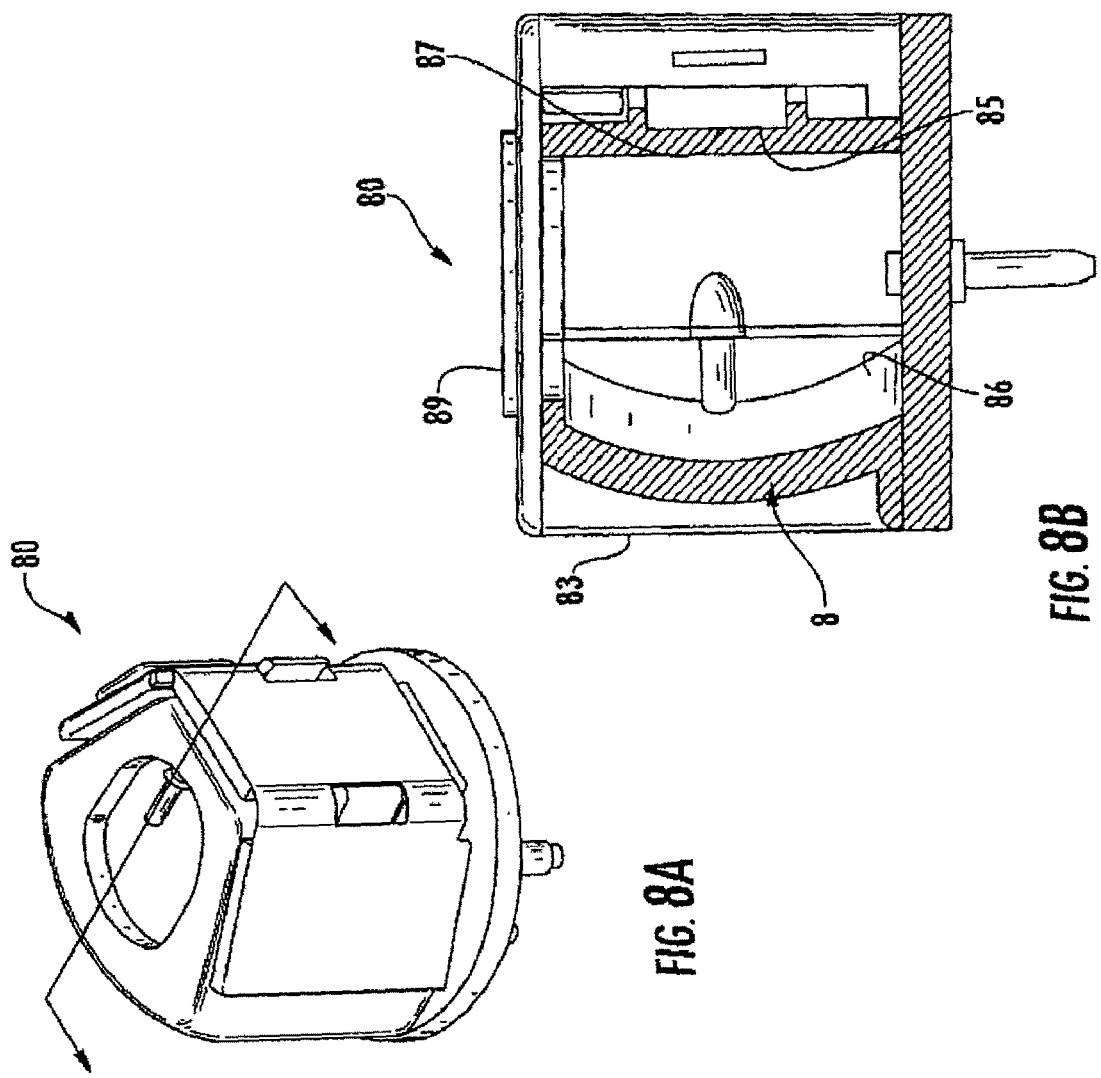

ABSORPTION SPECTROSCOPY APPARATUS AND METHOD

CROSS REFERENCE TO RELATED APPLICATIONS

This application claims benefit of Provisional Application No. 60/923,387 filed Apr. 13, 2007 and Provisional Application No. 60/931,463 filed May 22, 2007, each of which is incorporated herein by reference in its entirety.

FIELD OF THE DISCLOSURE

The present disclosure relates generally to spectrophotometric techniques for analyzing the content of a given fluid and, more particularly, to optimizing the sensitivity of such analysis. Even more particularly, the present disclosure relates to a new and improved multi-pass sample cell for use in absorption spectroscopy and an absorption spectroscopy apparatus incorporating the cell.

BACKGROUND OF THE DISCLOSURE

Spectroscopy systems and methods are used to analyze the composition of various types of materials, including gases, liquids and the like. Spectroscopy is based on the fact that different chemical compositions absorb energy, e.g., light, at different frequencies, so that measuring the intensity versus the frequency of the light passed through a sample can be used to identify which light frequencies were absorbed by the sample and which were not. Thus, the chemicals present in the sample can be readily identified. Spectroscopy systems and methods also can identify the amount of light absorbed by the sample at each given frequency. Thus, the quantity of each chemical present in the chemical composition can be determined. In addition, such analysis can be performed with any one of various different ranges of light such as infrared, ultraviolet and the like, each of which pertains to a separate range of frequencies.

An absorption cell (or resonator), which holds the gas or liquid sample through which light is passed, is used to perform spectroscopy analysis in conjunction with suitable spectroscopy equipment, such as a collimated laser light and a light detector. It has long been realized that to increase the sensitivity in providing both quantitative and qualitative analyses, the collimated laser light must be passed through a very large percentage of the available sample. Thus, absorption cells have been provided with "folded" light paths, in which mirrors reflect the light back and forth within the cell, such that the light makes multiple passes through the sample. The folded light path increases the optical path length between the laser and the light detector to thereby increase the sensitivity of a spectroscopy system incorporating an absorption cell producing a folded light path. Examples of existing "multi-pass" absorption cells are shown in U.S. Pat. Nos. 4,322,621; 4,749,276; 5,220,402; 5,440,143; 5,459,566; 5,485,276; 5,714,759; 5,731,583; 5,726,752; 5,818,578; and 5,949,537.

U.S. Pat. Nos. 6,373,056 and 6,528,792, commonly owned by the assignee of the present application, disclose a spectroscopic sensor system whereby the hot filament source also acts as its own bolometric sensor. This requires the emitted light to be returned to the source/bolometer itself, a unique condition not found in other spectroscopic systems. The optical cell detailed in both filings disclose an apparatus containing at least three functional elements, a source/bolometer, a return reflector, and a driver/detector where the optical cell occupies the space between the source/bolometer and the return reflector. The return reflector in both filings is either a flat or contoured mirror that returns at least some of the light back to the source. Therefore the light passes twice through the optical cell, once on its way from the source/bolometer to the return reflector and a second time on its way back from the return reflector to the source/bolometer.

What is still desired is an improved multi-pass sample cell for use in absorption spectroscopy that returns the light back to the source. This would be compatible with the hot self bolometer apparatus as detailed in U.S. Pat. Nos. 6,373,056 and 6,528,792 but would have applicability with other optical systems as well. Among other advantages and aspects, the new and improved multi-pass sample cell preferably will allow an absorption spectroscopy apparatus incorporating the cell to use light sources that are not collimated. In addition, the new and improved multi-pass sample cell preferably will minimize the difference (dispersion) in path lengths experienced by angularly divergent light rays traversing the sampling cell. The new and improved multi-pass sample cell preferably will also maintain or improve path length and throughput efficiency. Moreover, the new and improved multi-pass sample cell preferably will allow very high gas flow through the sampling cell while causing minimum disruption and turbulence to the gas flow. Furthermore, an absorption spectroscopy apparatus incorporating the new and improved multi-pass sample cell preferably will have a smaller total package size, including the source/bolometer, the optical cell, the driver/detector and the return reflector in order to fit into small footprint industry standard packaging.

SUMMARY OF THE DISCLOSURE

The present disclosure provides a new and improved multi-pass sample cell and an absorption spectroscopy apparatus incorporating the cell. An exemplary embodiment of the sample cell includes an elliptical mirror, centered on the midpoint between a source/detector and a mirror. The cavity between the elliptical mirror and the source/bolometer and mirror defines the optical sample cell. The light travels in a four segment path starting from the source/bolometer to the elliptical mirror, reflects off the elliptical mirror and travels to the mirror, reflects off the mirror and travels back to the elliptical mirror and finally reflects off the elliptical mirror and returns to the source/bolometer.

Among other benefits, the improved absorption spectroscopy apparatus of the present disclosure enables light to be passed through a substantial percentage of a sample passing through the sample cell. The cell is constructed so as to be small and compact while nonetheless enabling the light to make successive passes through the sample. The elliptical mirror minimizes differences (dispersion) in path lengths experienced by angularly divergent rays traversing through the sampling cell by refocusing the divergent light, while increasing path lengths and increasing throughput efficiency. Moreover, the sample cell of the present disclosure greatly relaxes the alignment tolerance between the source/bolometer and the multi-pass sample cell, a common problem in multi-pass absorption cell designs. The sample cell of the present disclosure improves the path length, efficiency and apparatus size of the hot self bolometer spectroscopic system.

According to one embodiment of the sample cell of the present disclosure, the mirror is larger than the source/bolometer and the degree to which the mirror is larger defines the alignment tolerance required between the source/bolometer and the multi-pass sample cell. According to another embodiment, the elliptical mirror can be the degenerate case, a spherical mirror.

In an additional embodiment of the sample cell the mirror can be mounted on a window that separates the source/bolometer from the multi-pass cell.

In an additional embodiment of the absorption spectroscopy apparatus the apparatus contains multiple source/bolometers. The multi-pass cell independently returns light from each source/bolometer back to that same source/bolometer without crossing light from one source/bolometer onto another source/bolometer. The plurality of source/bolometers can be arranged along the long axis of the elliptical mirror but other arrangements are possible.

In an additional embodiment of the absorption spectroscopy apparatus the cell is confined into a cylinder containing source/bolometer, elliptical mirror and the mirror.

In another aspect, an absorption spectroscopy apparatus includes a sample cell defining a sample volume. The sample cell includes an elliptical contoured mirror and a source/bolometer disposed opposite to the elliptical contoured mirror. The source/bolometer is positioned to emit electromagnetic radiation toward the elliptical contoured mirror. Another mirror is disposed opposite to the elliptical contoured mirror. The other mirror is configured to reflect electromagnetic radiation received from the elliptical contoured mirror back toward the elliptical contoured mirror. In operation, light emitted by the source/bolometer travels along more than one optical path through the sample volume, the multiply reflected light being reflected back toward the source/bolometer.

These and other advantages and aspects of the present disclosure will become apparent to those skilled in the art after a reading of the following description of exemplary embodiments when considered with the drawings.

BRIEF DESCRIPTION OF DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. In addition, x, y, and z coordinates are illustrated in some of the drawings for reference only.

FIG. 8A is a top perspective view of an absorption spectroscopy apparatus adapted for integration in a cylindrical cavity.

FIG. 8B is cross-sectional view of the device of FIG. 8A along A-A'.

FIG. 8C is top perspective view of a cylindrical cavity adapted to house the absorption spectroscopy apparatus of FIG. 8A.

DETAILED DESCRIPTION OF EXEMPLARY EMBODIMENTS

Figure 1:
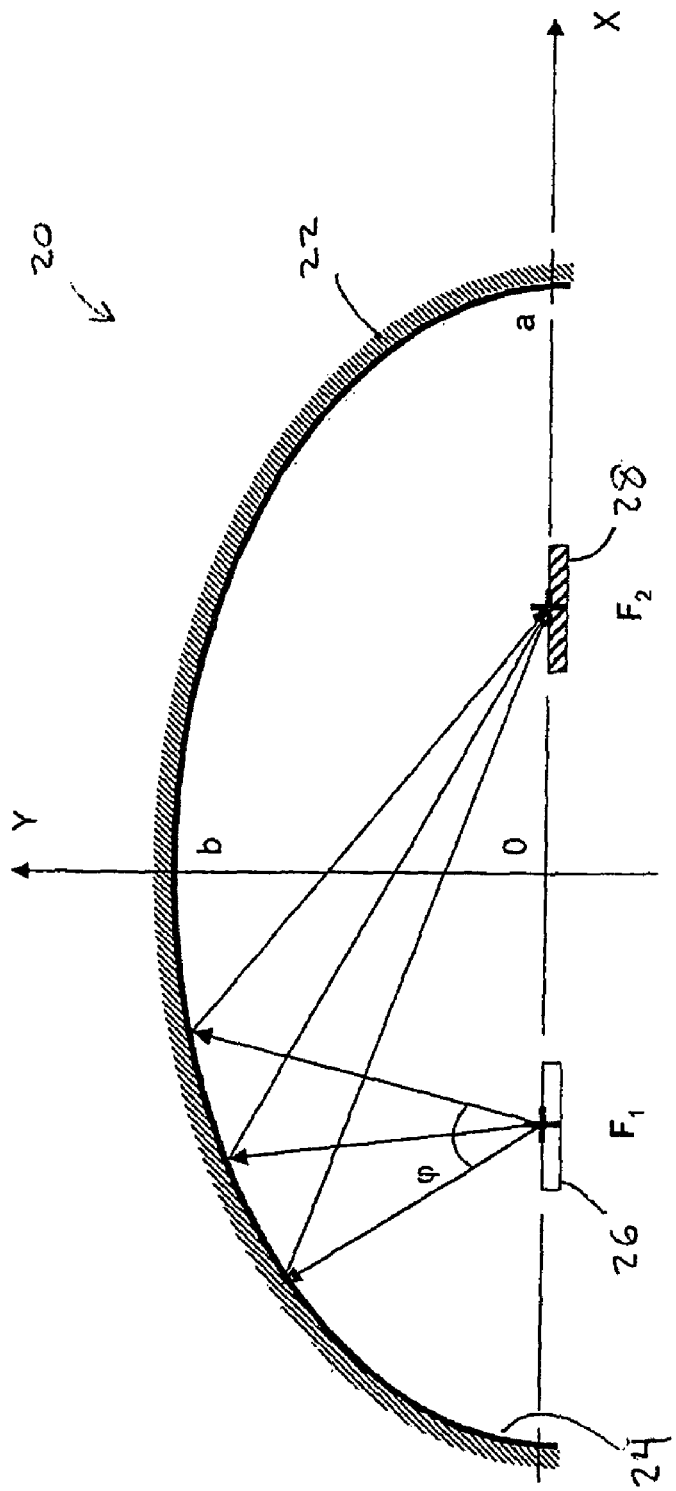
FIG. 1 is a schematic diagram illustrating a longitudinal cross-section view of an exemplary embodiment of an improved absorption spectroscopy apparatus constructed in accordance with the present invention.

Referring to FIG. 1 of the drawings, there is shown a schematic representation of an exemplary embodiment of a new and improved absorption spectroscopy apparatus 20 constructed in accordance with the present disclosure. The apparatus 20 includes a source/detector 26, a first elliptical reflector 22 defining an elliptical mirrored surface 24, and a second reflector 28. As shown, the source/detector 26 is positioned along one half of a plane bisecting the elliptical reflector 22. A second reflector 28 is positioned along the other half of that plane. Electromagnetic radiation is emitted from the source/detector 26 into a broad region. Three exemplary rays are shown emanating from the source/detector 26 covering an angle φ. With the source/detector 26 positioned at or near a first focus point $F_1$ of the elliptical reflector 22 and the second reflector 28 positioned at a second focus point $F_2$ of the same elliptical reflector 22, the divergent rays are substantially focused onto the second reflector 28. In some embodiments, the second reflector 28 is a planar reflecting surface.

Figure 2:
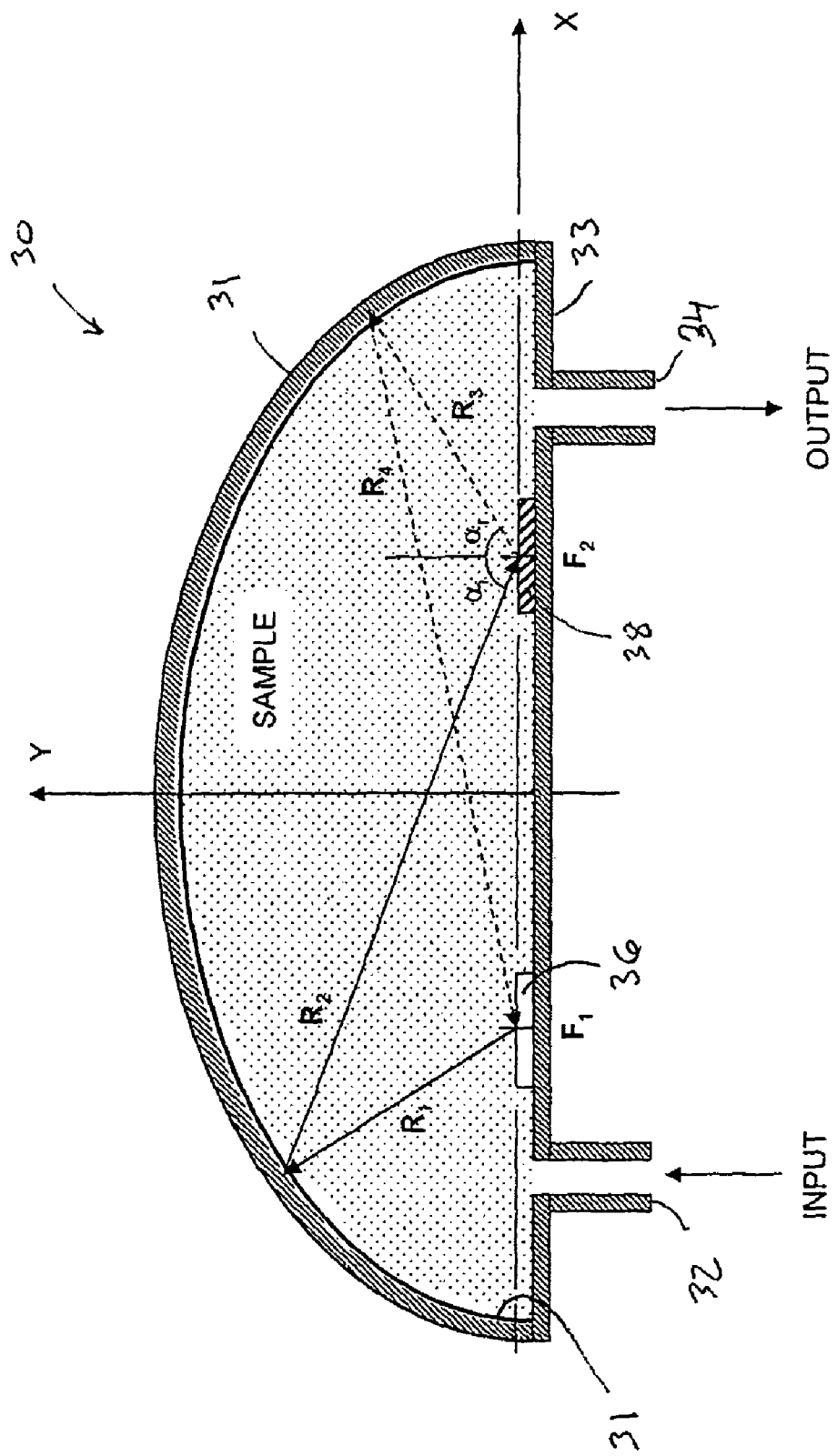
FIG. 2 is a schematic diagram illustrating a longitudinal cross-section view of an alternative embodiment of an improved absorption spectroscopy apparatus constructed in accordance with the present invention, illustrating an optical path of the light through the cell.

An alternative embodiment of a multi-pass sample cell 30 is shown in FIG. 2. The sample cell 30 again includes a source/detector 36 and second reflector 38 positioned at respective focal points $F_1$, $F_2$ of an elliptical reflector 31. In some embodiments, the device 30 includes an enclosing wall 33 forming an enclosed sample volume together with the elliptical reflector 31. One or more fluid ports 32, 34 can be provided to allow access to the enclosed sample volume. For example, an inlet port 32 and an outlet port 34 provide a flow path for continuous fluid or gas flow through the sample volume.

As also shown in FIG. 2, electromagnetic radiation (e.g., light) is emitted from the source/detector 36 and travels through the sample cell 30 along an exemplary ray $R_1$ impinging upon the elliptical reflective surface 31. The light is reflected off of the elliptical reflective surface 31 along a once-reflected ray $R_2$ and is refocused onto the second reflector or mirror 38 after traveling through the interior volume of the sample cell (optical sample cell). The once-reflected light is reflected off of the mirror 38 along a twice-reflected ray $R_3$ traveling again through the interior volume of the optical sample cell 30 to the elliptical reflective surface 31. Finally, the twice-reflected light reflects off of the elliptical reflective surface 31 along a thrice-reflected ray $R_4$ being ultimately refocused back on the source/detector 36. The rays $R_1, R_2, R_3, R_4$ illustrated in FIG. 2 are representative of one of many optical paths that the electromagnetic radiation travels within the cell 30 between the same source/detector 36 and mirror 38. The source/detector 36 can be a source/bolometer, such as an incandescent light source with large angularly divergent emission pattern.

The elliptical mirrors 22, 31 shown in FIG. 1 and FIG. 2 are shown in cross section, each mirror 22, 31 being a three dimensional object. In some embodiments, the contour of the mirror is a section of an ellipsoid defined by the following generic equation where $2a$ is the long axis of the ellipse, $2b$ is the short axis of the ellipse and $2h$ is the distance between foci. To generate a three-dimensional surface of the mirror, this contour is rotated about the long axis.

$$\frac{x^2}{a^2} + \frac{y^2}{b^2} = 1 \tag{1}$$

$$a^2 = b^2 + h^2 \tag{2}$$

Among other aspects and benefits, the new and improved absorption spectroscopy apparatus 20, 30 of the present disclosure enables electromagnetic radiation, such as visible and/or infrared light, to be passed through a substantial percentage of a sample passing through the sample cell 20, 30. In some embodiments, the cell 20, 30 is constructed to be small and compact (e.g., not more than about 10 cm in diameter), while nonetheless enabling the radiation to make successive passes through the sample between emission and detection at the source/detector 26, 36. The elliptical mirror 22, 31 minimizes the differences (dispersion) in path lengths experienced by angularly divergent rays traversing through the sampling cell 20, 30 by refocusing the light, while at the same time increasing path lengths and increasing throughput efficiency. Moreover, the sample cell 20, 30 of the present disclosure can capture and return light from a highly disperse source and does not require a collimated source.

In general, an ellipsoidal surface is a locus of all points disposed about two foci $F_1, F_2$, where the sum of the distances from each point along the surface to $F_1$ and $F_2$ is a constant. With an ellipsoidal surface, radiation from a radiation source (collimated or wide angle) from $F_1$ toward the surface is reflected by the surface and is focused at $F_2$. The propagation path length from all angles of the radiated light is substantially equal. Thus, an equal amplitude wide angle source can cover substantially the entire volume of the cell, thereby improving sampling efficiency of a sample within the cell.

In a preferred form of the invention, a source/detector (bolometer) is provided at $F_1$ and a mirror is provided at $F_2$, such that substantially all radiation incident on the mirror at $F_2$ is reflected back to the source/bolometer at $F_1$. Thus, only a single source/bolometer is necessary. In some embodiments, a second source/bolometer is placed at $F_2$ in place of the mirror. The two source/bolometers can each be tuned to the same wavelength and act in pairs: the first source/bolometer at $F_1$ radiates to the second source/bolometer at $F_2$; whereas, the second source/bolometer at $F_2$ radiates to the first source/bolometer at $F_1$. Preferably, the emission detection characteristics of each of the first and second source/bolometers are substantially matched. Such matching can be accomplished by fabricating each device on the same substrate. The substrate can be severed to facilitate separation of the two source/bolometers. In some embodiments, the first and second source/bolometers are tuned to different wavelengths.

Figure 3:
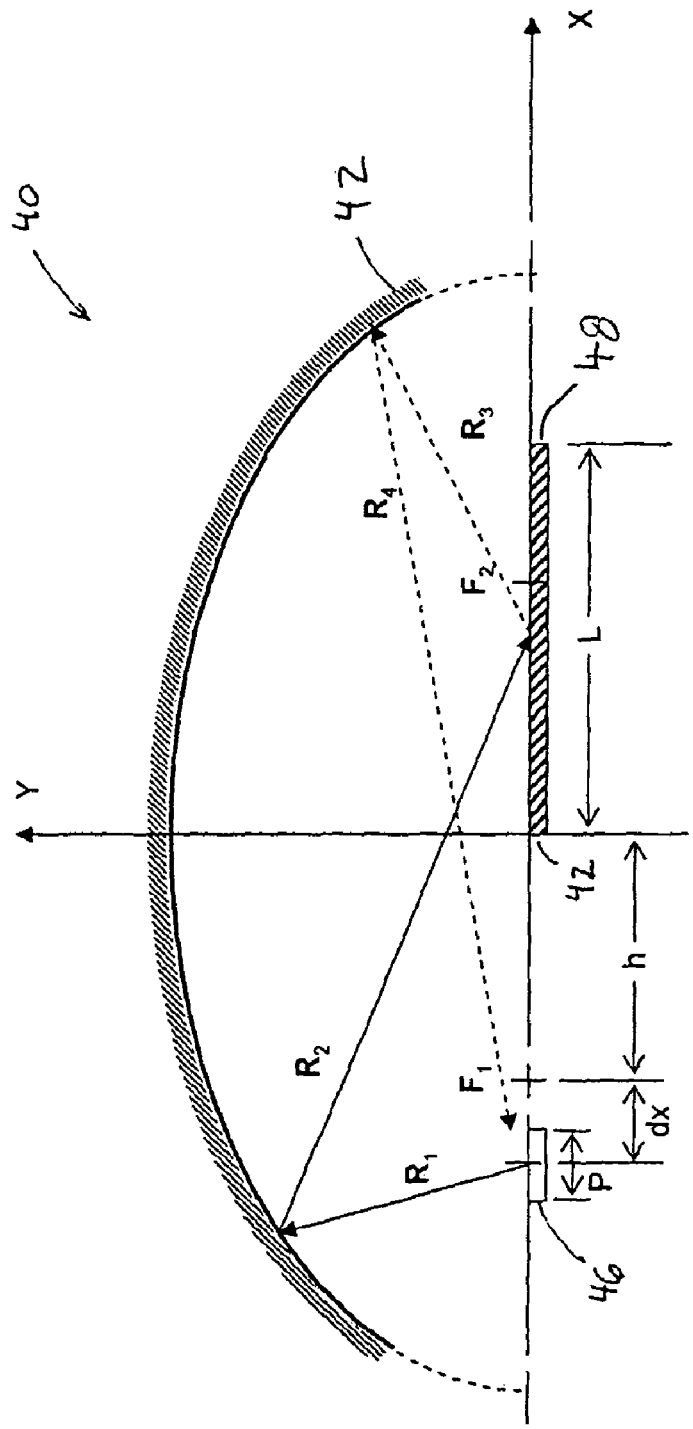
FIG. 3 is a schematic diagram illustrating a longitudinal cross-section view of an exemplary embodiment of an absorption spectroscopy apparatus showing a substantial alignment tolerance.

As shown in FIG. 3 an improved absorption spectroscopy apparatus 40 provides a very high tolerance to misalignment. The degree of misalignment or alignment tolerance, dx, can be best represented by equation 3 where L represents the size of the mirror 48, h is the distance from the center of the ellipse 42 to one of the two foci and P is the size of the source/bolometer 46. When L is much larger than h and P the alignment tolerance dx is large. In the extreme case, L can be the entire distance between the center and the pole of the ellipse. FIG. 3 is shown in two dimensions, but this relationship holds in three dimensions.

$$dx = L - h - \frac{P}{2} \tag{3}$$

Figure 5:
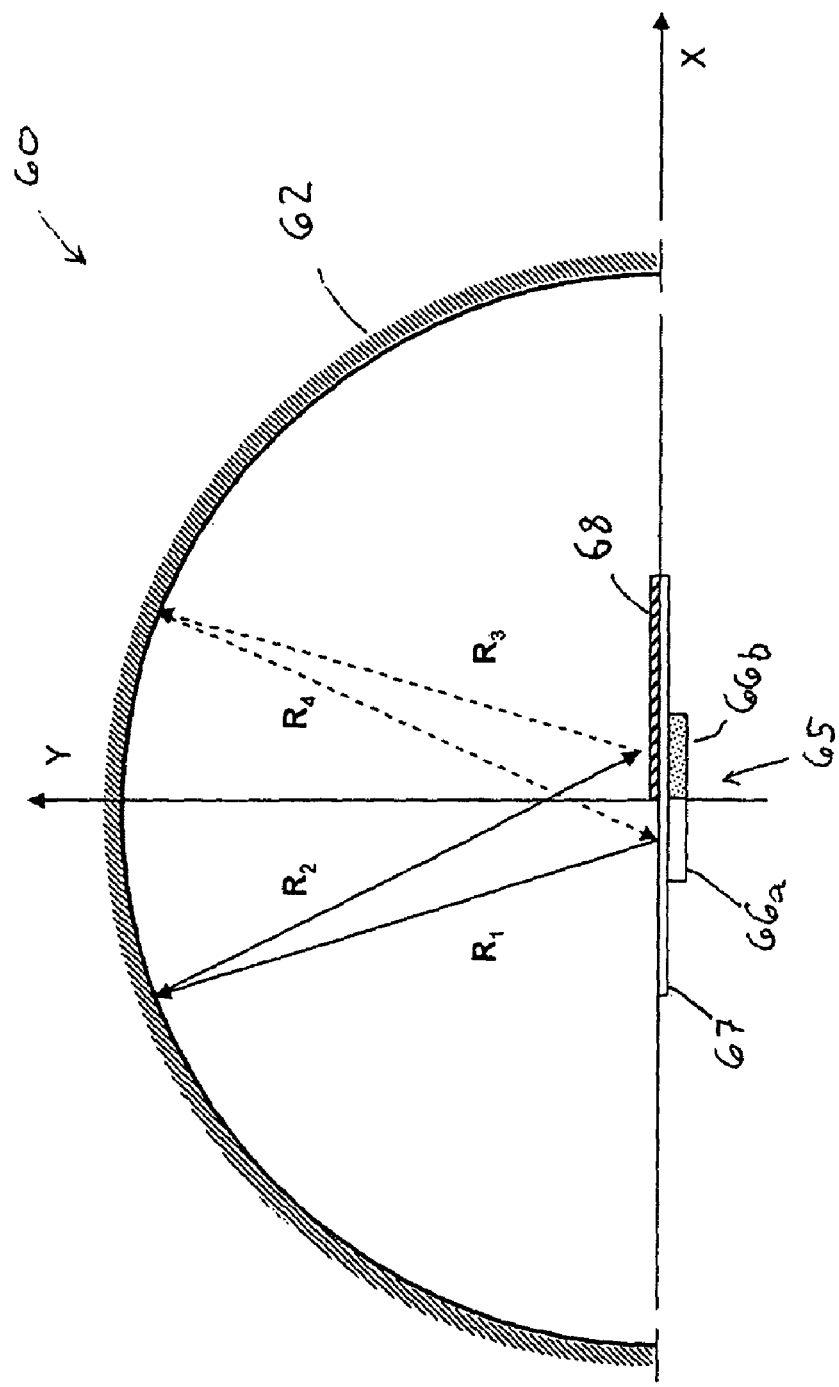
FIG. 5 is a schematic diagram illustrating a cross-section view of a spherical embodiment of absorption spectroscopy apparatus including a window separating the source/bolometer from the sample cell and the mirror mounted on the window.

In an exemplary embodiment of the invention shown in FIG. 5, the elliptical mirror is a spherical mirror, the degenerate case when h=0. For this case, the equation 3 for the alignment tolerance dx still holds true. As illustrated, a source/bolometer 65 is positioned substantially at the center of a spherical reflector 62 and adjacent to a mirrored reflector 68. Each of the source/bolometer 65 and mirror 68 can be disposed along a respective side of a central point, equidistant to the locus of points along the spherical reflector 62. In some embodiments, the source/bolometer 65 represents a first pixel 66a, positioned adjacent to a second pixel 66b. The second pixel 66b can be used as a reference. In some embodiments, the second pixel 66b can be covered, or "blinded" from the sample volume to serve as a reference for identifying and removing device contributions from measurement results. As illustrated, the second pixel 66b can be blinded by the mirror 68.

As shown in the exemplary embodiment of FIG. 5, the source/bolometer 66a, 66b can be separated from a sample volume of the sample cell 60 by a window 67. This configuration 60 prevents sampling fluids or gasses from contacting the source/bolometer 66a, 66b directly. In some embodiments, the window 67 can serve as a mounting surface for a mirror 68.

Figure 6:
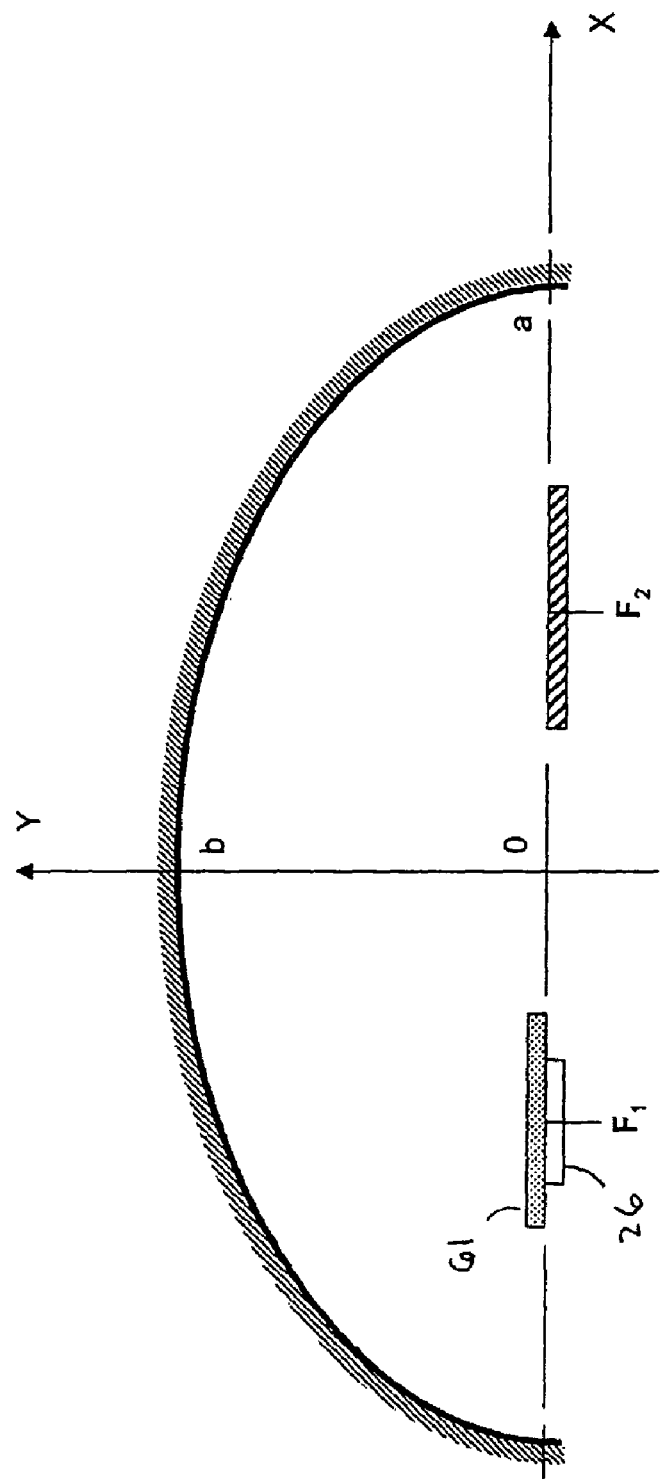
FIG. 6 is a schematic diagram illustrating a cross-section view of an additional exemplary embodiment of an improved absorption spectroscopy apparatus including an optical filter between the source/bolometer and the multi-pass cell.

In another exemplary embodiment of the invention, referring now to FIG. 6, an optical filter 61 is positioned in the optical path between the source/detector 26 and the sample volume in order to filter the electromagnetic radiation emitted/sensed by the source/detector 26. For example, the optical filter 61 can be positioned just above the source/detector 26. In other embodiments, the optical filter 61 can be positioned anywhere throughout the optical path. When appropriately tuned, the filter 61 facilitates selection of a narrow spectral band for specific spectroscopic chemical analysis.

Figure 4:
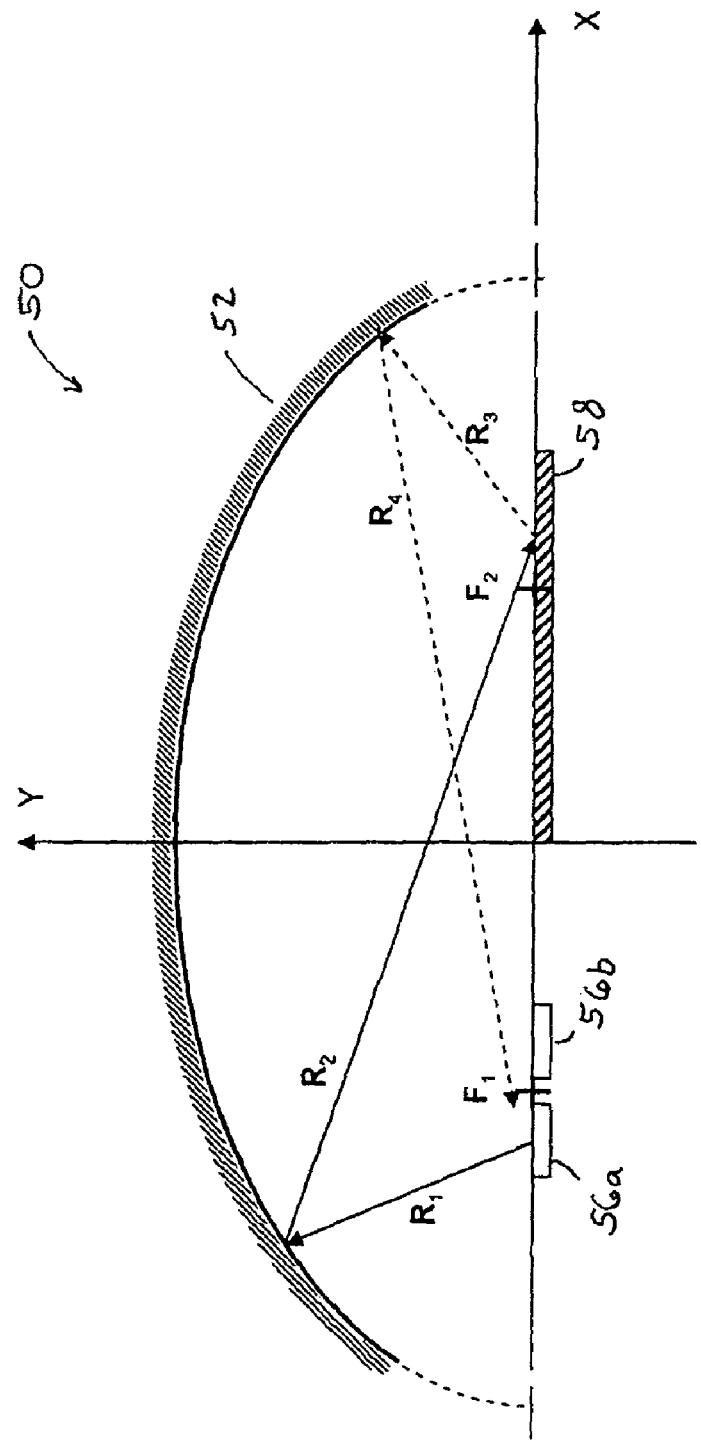
FIG. 4 is a schematic diagram illustrating a longitudinal cross-section view of another alternative embodiment of an absorption spectroscopy apparatus including multiple source/detector elements.

In the exemplary embodiment of the invention, referring now to FIG. 4, multiple source/bolometers can be positioned in one half of the bisecting plane of an elliptical mirror 52. In a two pixel example, the first and second source/bolometers 56a, 56b are positioned along a central axis of the elliptical mirror 52. This representation is one of many possible configurations and was chosen to best demonstrate the functional state. Light from each of the source/bolometers 56a, 56b radiates into the interior volume of the sample cell 50 and onto the elliptical mirror 52. The elliptical mirror 52 reflects the light and refocuses that light down onto the mirror 58 where an inverted image forms. The image reflects off of the mirror 58 and passes back through the interior volume of the sample cell 50 and onto the elliptical mirror 52. Once again the light reflects off the elliptical mirror 52 and is refocused back onto the array of source/bolometers 56a, 56b. Because a positive image forms in the bisecting plane, light from each individual source/bolometer 56a, 56b returns specifically back to that same source/bolometer 56a, 56b without significant crossover to neighboring source/bolometers 56a, 56b. This maintains specificity between the individual source/bolometers 56a, 56b. If each source/bolometer 56a, 56b is tuned to a different spectral waveband, different spectroscopic measurements can be made in parallel at the same time in the same sample cell 50 on the same sample fluid.

Figure 7:
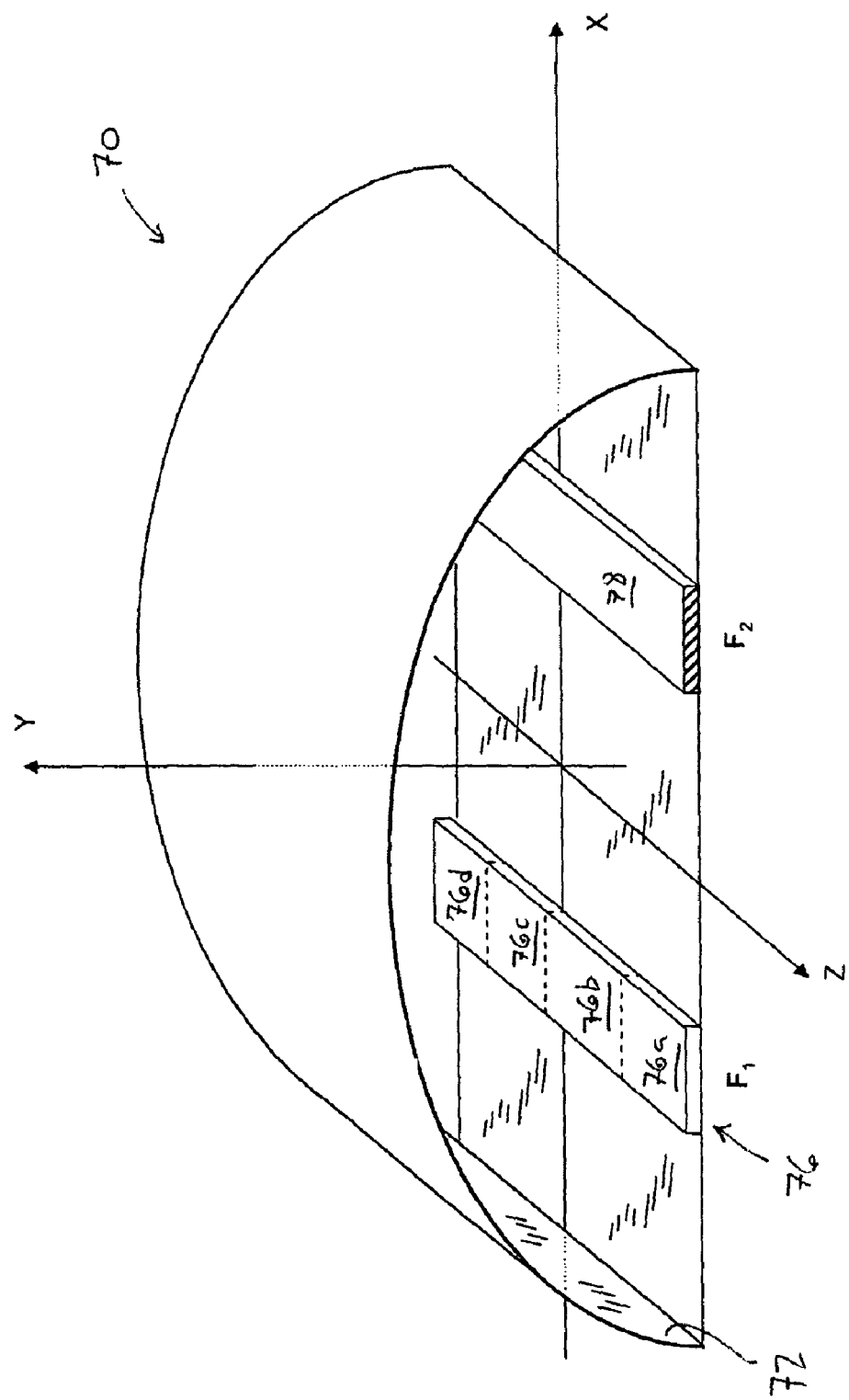
FIG. 7 is a schematic diagram illustrating a perspective view of an embodiment of an improved absorption spectroscopy apparatus including multi-pass cell including a semi-elliptical cylinder.

In some embodiments, a cylindrical sample cell can be formed having an elliptical reflective surface defining at least a portion of an elliptical cylinder. Such an embodiment can be formed by extending the reflective surface of any of the embodiments shown in the preceding figures along an axis perpendicular to the page. A perspective view of a semi-elliptical cylindrical cavity 70 is shown in FIG. 7. An a reflective surface 72 extending for a distance along the z axis, forms an elliptical cross section parallel to the x-y plane. One or more source/detectors 76 can be located along a first line extending along a first focus $F_1$ of the elliptical surface. The source detector 76 can be an extended linear (i.e., line) source or single pixel, or an array of more than one source detectors, or pixels 76a, 76b, 76c, 76d disposed along the focal line $F_1$, as shown. A mirror 78 is disposed along a second line extending along a second focus $F_2$ of the elliptical surface 72. The mirror 78 need not be confined to the line as shown, but can extend over a more substantial region to improve device manufacturing tolerances. Electromagnetic radiation from the source/detector 76 reflects once off of the elliptical surface 72 onto the mirror 78, where it is reflected back onto the elliptical surface 72, where it reflects again toward the source/detector 76. This arrangement can include a section of a right circular cylinder in which the source/detector 76 and mirror 78 are each disposed about a central axis of the cylinder.

In some embodiments, the multi-pass sampling apparatus can be configured to fit into a confined volume. Referring to FIG. 8A, FIG. 8B and FIG. 8C, an exemplary embodiment of the invention 80 is adapted to fit within a sample cylinder 82. In this configuration, the boundary of an elliptical mirror 81 is defined at least in part by a lateral wall 83 of the cylinder 82. A surface of the elliptical mirror 86 is positioned in a vertical direction within the cylinder 82 such that the curvature of the elliptical mirror 86 fits within the curvature of the walls 83 of the cylinder 82. A source/bolometer 85 and the mirror 87 are positioned on the opposite side of the cylinder 82. A top opening 89 of the cylinder 82 provides an inlet for sample fluids to diffuse in and out of the sample cell 80.

Figure 9:
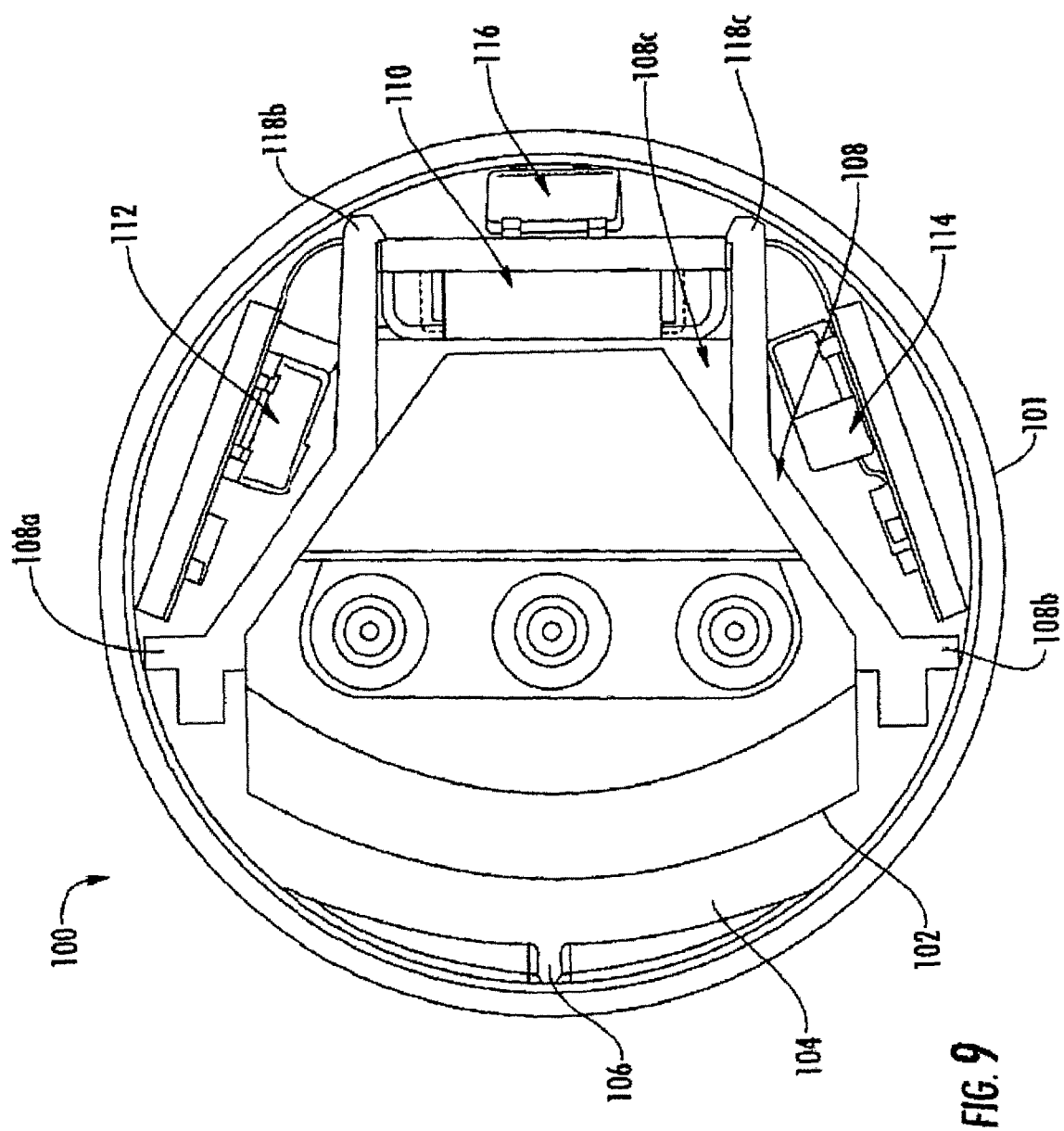
FIG. 9 is a top sectional view of an exemplary embodiment of an absorption spectroscopy apparatus according to the invention.

Referring to FIG. 9, a top sectional view of an alternative exemplary embodiment of an absorption spectroscopy apparatus is shown. A gas or fluid sample cell 100 includes a housing 101 including an elliptical mirror having an interior mirrored surface 102 and a supporting frame 104. The supporting frame 104 is preferably formed from a rigid material, such as a plastic or metal having sufficient thickness to ensure uniformity of the elliptical mirrored surface 102 during use in its intended environment. The supporting frame 104 can be formed of plastic using an injection molding process, with a mirrored surface 102 applied in a separate thin film process. The mirrored surface 102 can be applied by a painting process, using thin film deposition, or otherwise attaching a reflective surface. Intended environments can include high temperatures or substantial temperature variations. To ensure rigidity, one or more structural supporting members or ribs can be included. The exemplary embodiment includes a vertical rib 106 extending along a rear vertical dimension of the center of the elliptical mirror.

The device 100 includes a second frame member 108 placed at least partially in apposition to the mirrored surface 102. An emitter sensor 110 is fixedly attached with respect to the second frame member 108. To ensure precise positioning of the emitter sensor 110, at least within a design tolerance, the frame member 108 provides an alignment function. Thus, the frame member 108 ensure the relative positioning of the emitter/sensor 110 is maintained with respect to the mirrored surface 102. In some embodiments, the frame member 108 includes an emitter/sensor mount 108c and lateral frame extensions 108a, 108b. The lateral frame extensions 108a, 108b extend from the emitter/sensor mount 108c to the mirror supporting frame 104. Thus, proper positioning of the emitter/sensor 110 and mirrored surface 102 can be controlled to some degree by manufacturing processes of the frames 104, 108. In some embodiments, the frame 108 is formed having vertical walls to laterally contain a sample volume together with the mirror frame 104.

One or more electronic modules can be positioned in a volume defined between exterior surface of walls of the frame member 108 and adjacent interior surface of the housing 101. In the exemplary embodiment, a first drive/sense electronics module 112 is positioned behind a right frame extension 108a, a drive/sense electronics module 114 is positioned behind a left frame extension 108b, and emitter sensor electronics 116 is positioned behind the emitter/sensor mount 108c. As shown, the frame member 108 includes posterior frame extension clips 118a, 118b adapted to keep the emitter sensor module in a fixed relation to the emitter/sensor mount 108c.

Figure 10:
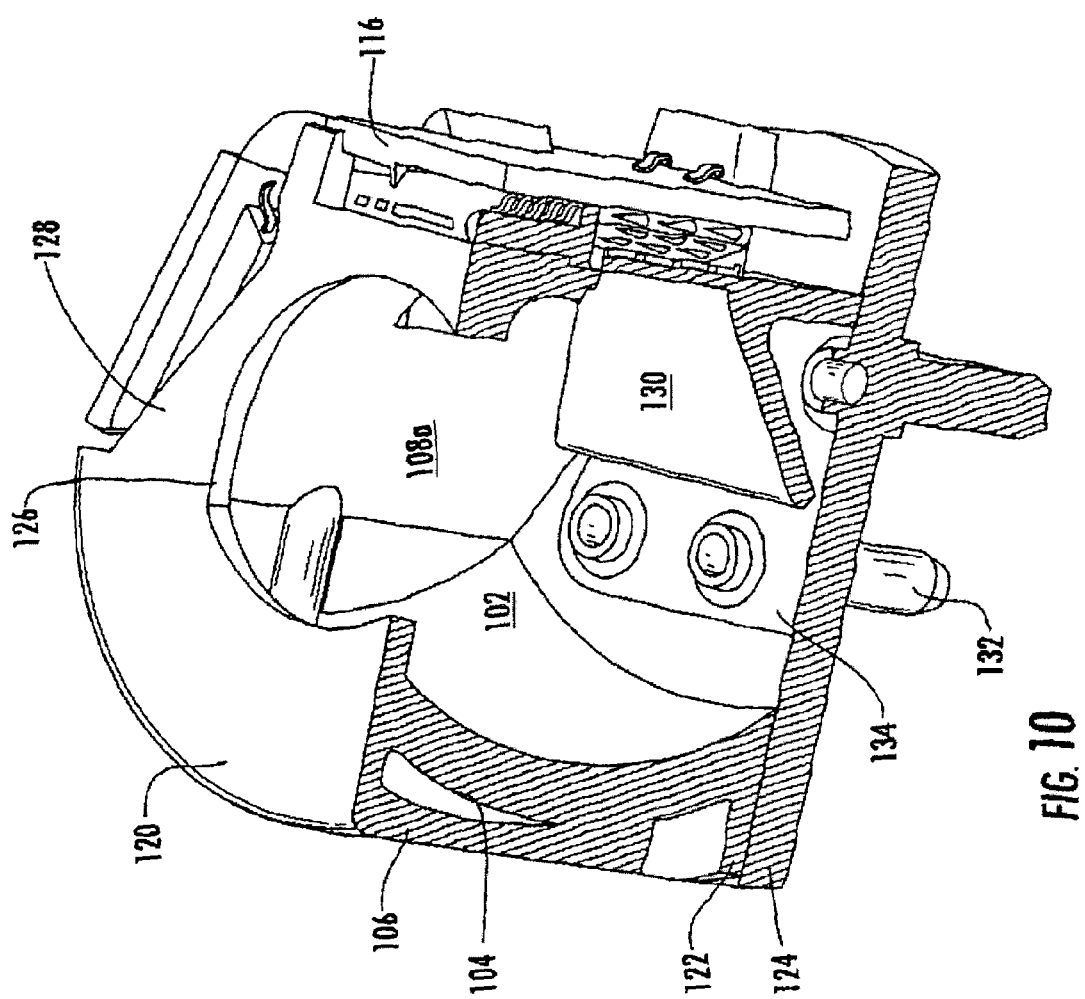
FIG. 10 is a top perspective view of an exemplary embodiment of the absorption spectroscopy apparatus of FIG. 9 shown in cross section.

Referring to FIG. 10, a top perspective view of an exemplary embodiment of the gas or fluid sample cell 100 is shown in cross section. The mirror supporting frame 104 includes a first top support member 120 and a bottom support member 122. The frame members 104, 108 are seated on a bottom wall 124, defining a bottom surface of the sample volume. In some embodiments, the bottom wall 124 is a printed circuit board. In other embodiments, the bottom wall 124 is an end-cap filter, adapted to keep particulates out of the sample volume. The bottom wall 124 can cover the entire bottom surface of the housing 101 as shown. The bottom support member 122 of the mirror supporting frame 104 provides a secure footing to position the mirrored surface 132 with respect to the bottom wall 124. The first top support member 120 defines at least part of a diffusive gas exchange port 126. The frame member 108 includes a second top support member 128 coplanar with the first top support member 120. The second top support member 128 also defines a portion of the diffusive gas exchange port 126. In some embodiments, a bottom ledge 130 extends below the emitter/sensor 110 between the emitter/sensor mount 108c and the bottom wall 124. The bottom ledge 130 is a sloping ledge remaining out of view from the emitter/sensor 110. One or more electrical contacts 132 extend through and beyond the bottom wall 124 providing external access to electronic assemblies 112, 114, 116. In some embodiments, a flex-print circuit 134 provides contact between the one or more electrical contacts 132 and the electronic assemblies 112, 114, 116.

Figure 11:
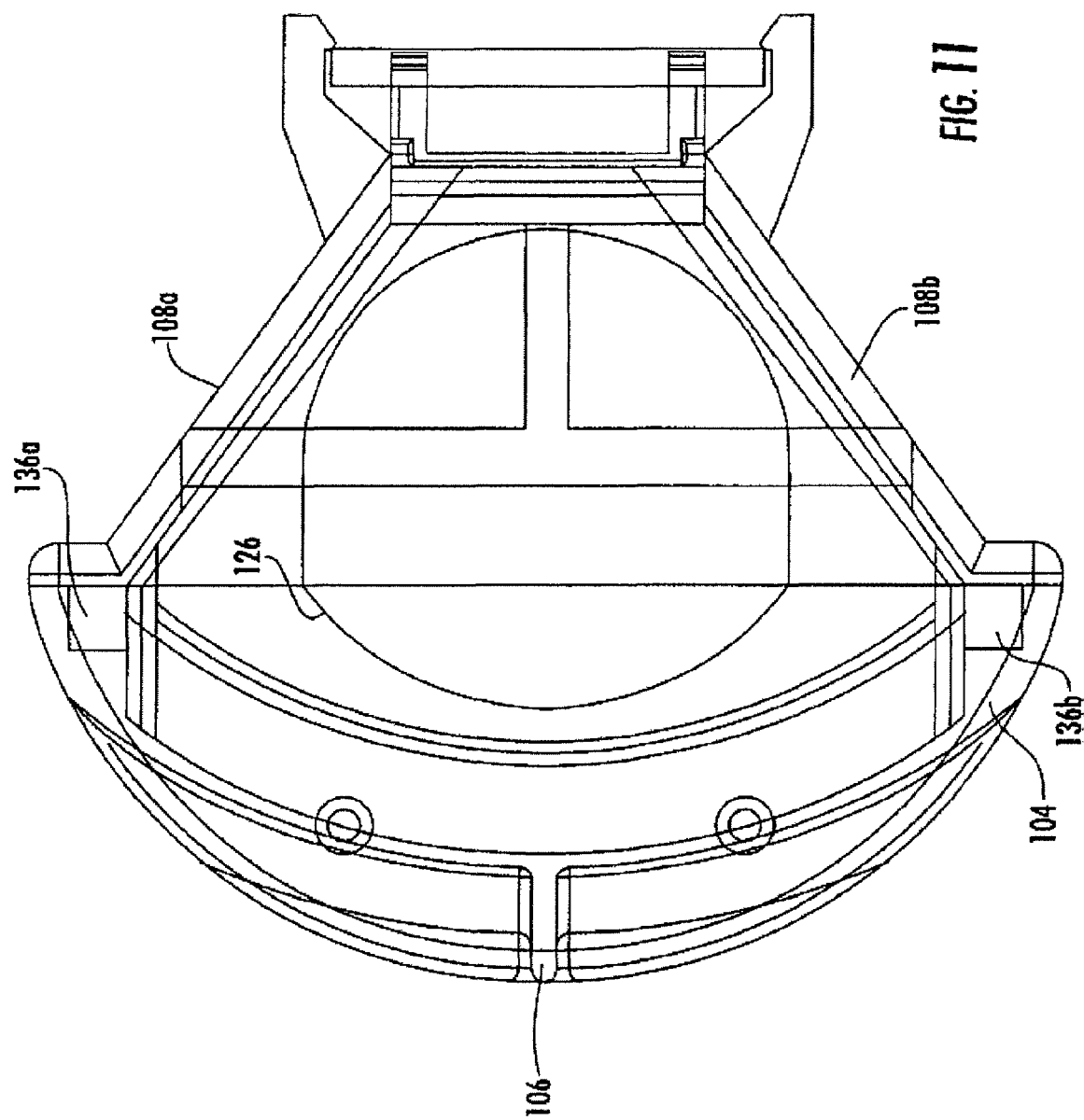
FIG. 11 is a top view of an exemplary embodiment of an absorption spectroscopy apparatus according to the invention with at least some of the surfaces shown in transparency.
Figure 12:
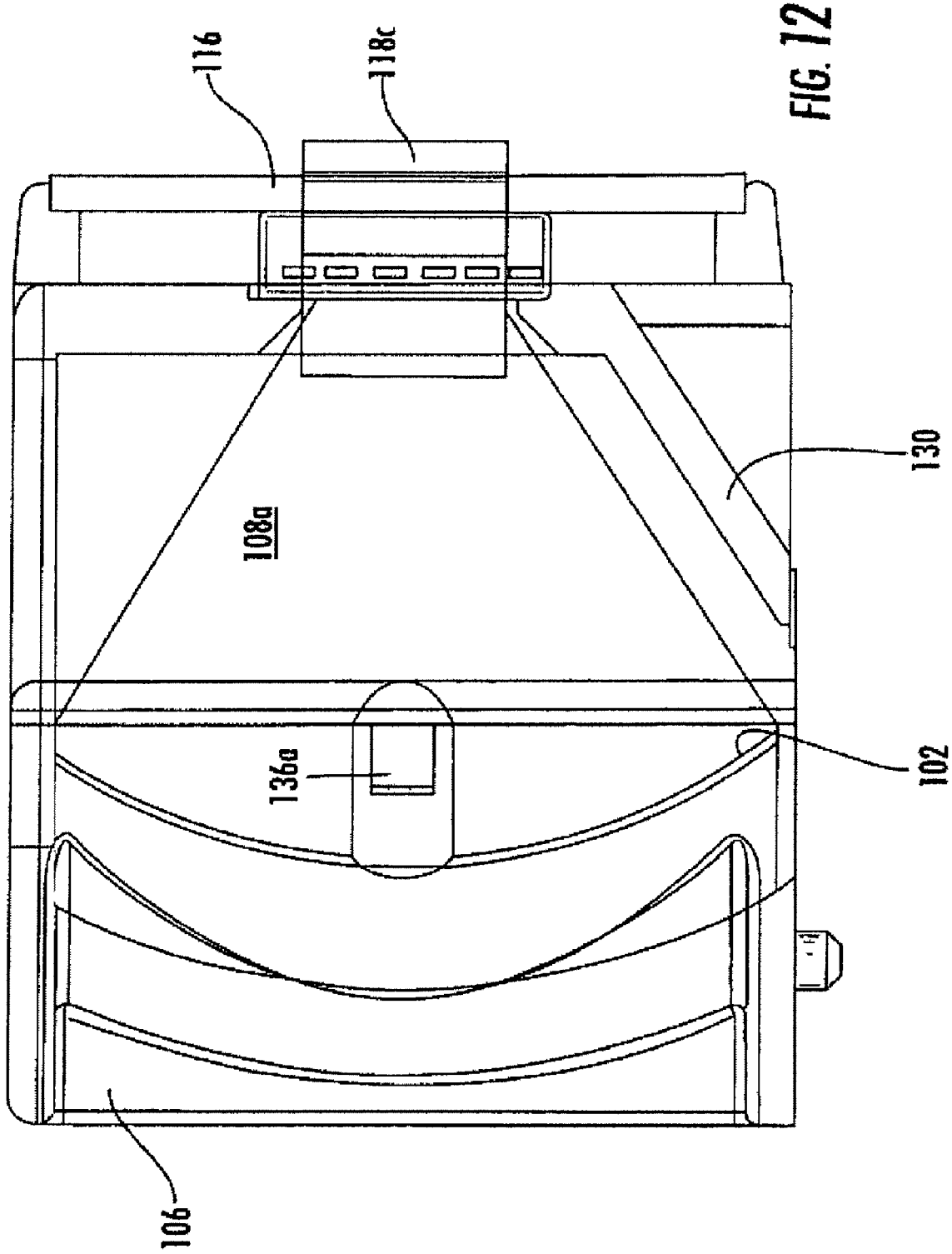
FIG. 12 is an elevation view of the absorption spectroscopy apparatus shown in FIG. 11 with at least some of the surfaces shown in transparency.

Referring to FIG. 11 and FIG. 12, top and side views of an exemplary embodiment of the gas or fluid sample cell 100 are respectively shown having at least some of the surfaces illustrated in transparency. In some embodiments, the lateral frame extensions 108a, 108b respectively include alignment pins 136a, 136b (generally 136). The alignment pins 136 are disposed to abut an adjacent surface of the mirrored surface 102 or frame 104, the abutment providing a desired spacing between the emitter/sensor mount 108c and the mirrored surface 132.

The present disclosure, therefore, provides an improved "multi-pass" sample cell that causes light to pass through a very large percentage of a sample contained in the cell. The improved sample cell prevents the loss of significant amounts of light through ends of the cell and increases the throughput of the cell. In addition, the improved cell is compact, robust, and relatively easy to manufacture.

Various embodiments of improved sample cell devices and methods of sampling have been described herein. These embodiments are given by way of example and are not intended to limit the scope of the present invention. It should be appreciated, moreover, that the various features of the embodiments that have been described may be combined in various ways to produce numerous additional embodiments. Moreover, while various materials, dimensions, shapes, source/detection and mirror locations, etc. have been described for use with disclosed embodiments, others besides those disclosed may be utilized without exceeding the scope of the present disclosure as recited in the following claims.

What is claimed is:

1. An absorption spectroscopy apparatus comprising:
a sample cell defining a sample volume including:
an elliptical contoured mirror;
a source/bolometer disposed opposite to the elliptical contoured mirror, the source/bolometer emitting electromagnetic radiation toward the elliptical contoured mirror; and
a mirror disposed opposite to the elliptical contoured mirror, the mirror configured to reflect electromagnetic radiation received from the elliptical contoured mirror back toward the elliptical contoured mirror, light emitted by the source/bolometer traveling along more than one optical path through the sample volume and being reflected back toward the source/bolometer.

2. The apparatus of claim 1, further comprising a window positioned between source/bolometer and the sample volume.

3. The apparatus of claim 2, wherein the mirror is mounted on a surface of the window between source/bolometer and the sample volume.

4. The apparatus of claim 1 further comprising an optical filter positioned between the source/bolometer and the elliptical contoured mirror.

5. The apparatus of claim 1 including a plurality of various-sized mirrors to increase alignment tolerance.

6. The apparatus of claim 1, wherein the elliptical contoured mirror in a degenerate case is a spherical mirror.

7. The apparatus of claim 1, where the light emitted from the source/bolometer is reflected three times within the sample cell before returning to the source/bolometer.

8. The apparatus of claim 1, further comprising a window separating the source/bolometer from the sample cell volume, wherein the mirror is mounted on an outer surface of the optical filter window.

9. The apparatus of claim 1, further comprising at least one other source/bolometer.

10. The apparatus of claim 9, where the source bolometer and at least one other source/bolometer are arranged in an array located along long axis of the elliptical contoured mirror.

11. The apparatus of claim 9, where the source bolometer and at least one other source/bolometer are arranged in an array along the bisecting plane of the elliptical mirror.

12. The apparatus of claim 9, wherein one of the at least one other source/bolometers is covered by the mirror, the covered source/bolometer serving as a reference to the source/bolometer.

13. An absorption spectroscopy apparatus comprising:
a sample cell confined to a cylindrical volume defining an interior sample volume including:
an elliptical contoured mirror;
a source/bolometer disposed opposite to the elliptical contoured mirror, the source/bolometer emitting electromagnetic radiation toward the elliptical contoured mirror; and
a mirror disposed opposite to the elliptical contoured mirror, the mirror configured to reflect electromagnetic radiation received from the elliptical contoured mirror back toward the elliptical contoured mirror, light emitted by the source/bolometer traveling along more than one optical path through the sample volume and being reflected back toward the source/bolometer.

14. The apparatus of claim 13, further comprising at least one aligning pin configured to align the elliptical contoured mirror with respect to the source/bolometer.

15. The apparatus of claim 13, further comprising an optical filter window positioned to separate the source bolometer from the sample volume, wherein the mirror is mounted on an outer surface of the optical filter window.

16. The apparatus of claim 13, further comprising a first fluid port providing external access to the sample volume through which a sample fluid can be transferred to the sample volume.

17. The apparatus of claim 16, further comprising a second fluid port providing external access to the sample volume, a fluid entering the sample volume through the first fluid port and exiting the sample volume through the second fluid port.

18. A method comprising:
providing a sample cell defining a sample volume including:
an elliptical contoured mirror;
a source/bolometer disposed opposite to the elliptical contoured mirror, emitting electromagnetic radiation from the source/bolometer toward the elliptical contoured mirror;
providing a mirror disposed opposite to the elliptical contoured mirror; and
using said mirror disposed opposite to the elliptical contoured mirror, reflecting electromagnetic radiation received from the elliptical contoured mirror back toward the elliptical contoured mirror such that light emitted by the source/bolometer travels along more than one optical path through the sample volume and is reflected back toward the source/bolometer.

19. The method of claim 18, wherein the sample cell defining a sample volume is confined to a cylindrical volume.

* * * * *